US00PP19299P2

(12) United States Plant Patent
Beers

(10) Patent No.: US PP19,299 P2
(45) Date of Patent: Oct. 7, 2008

(54) ***CELOSIA* PLANT NAMED 'ZANCELOR'**

(50) Latin Name: *Celosia argentea*
Varietal Denomination: Zancelor

(75) Inventor: Martinus Petrus Beers, Hoofddorp (NL)

(73) Assignee: Chrysanthemum Breeders Association Research B.V., Rijsenhout (NL)

( * ) Notice: Subject to any disclaimer, the term of this patent is extended or adjusted under 35 U.S.C. 154(b) by 0 days.

(21) Appl. No.: 11/881,792

(22) Filed: Jul. 27, 2007

(51) Int. Cl.
*A01H 5/00* (2006.01)

(52) U.S. Cl. ..... Plt./263.1
(58) Field of Classification Search ..... Plt./263.1
See application file for complete search history.

(56) References Cited

PUBLICATIONS

Upov–rom Plant Variety Database 2007/06 GTI Jouve Retrieval Software, Citation for Celosia 'Zancelor' one page.*

* cited by examiner

*Primary Examiner*—Kent L. Bell
*Assistant Examiner*—June Hwu
(74) *Attorney, Agent, or Firm*—C. A. Whealy

(57) ABSTRACT

A new and distinct cultivar of *Celosia* plant named 'Zancelor', characterized by its upright and compact plant habit; freely branching habit; freely flowering habit; orange-colored flowers arranged on dense plume-like spikes; and good garden performance.

2 Drawing Sheets

Botanical designation: *Celosia argentea.*
Cultivar denomination: 'Zancelor'.

BACKGROUND OF THE INVENTION

The present invention relates to a new and distinct cultivar of *Celosia,* botanically known as *Celosia argentea* and hereinafter referred to by the name 'Zancelor'.

The new *Celosia* is a product of a planned breeding program conducted by the Inventor in Hillegom, The Netherlands. The objective of the breeding program is to create new uniform and compact *Celosia* cultivars with attractive flower coloration.

The new *Celosia* originated from a self-pollination made by the Inventor in 2000 in Hillegom, The Netherlands of a proprietary selection of *Celosia hybrida* identified as code number 00014-2, not patented. The new *Celosia* was discovered and selected by the Inventor as a single flowering plant within the progeny of the stated self-pollination in a controlled environment in Hillegom, The Netherlands in 2001.

Asexual reproduction of the new *Celosia* by cuttings in a controlled environment in Rijsenhout, The Netherlands since 2001, has shown that the unique features of this new *Celosia* are stable and reproduced true to type in successive generations.

SUMMARY OF THE INVENTION

The cultivar Zancelor has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Zancelor'.

These characteristics in combination distinguish 'Zancelor' as a new and distinct cultivar of *Celosia:*

1. Upright and compact plant habit.
2. Freely branching habit.
3. Freely flowering habit.
4. Orange-colored flowers arranged on plume-like spikes.
5. Good garden performance.

Plants of the new *Celosia* differ from plants of the parent selection primarily in flower color and plant uniformity.

Plants of the new *Celosia* can be compared to plants of the cultivar Icecream Orange, not patented. Plants of the new *Celosia* and the cultivar Icecream Orange differ primarily in flower color as plants of the new *Celosia* had darker orange-colored flowers than plants of the cultivar Icecream Orange.

BRIEF DESCRIPTION OF THE PHOTOGRAPHS

The accompanying colored photographs illustrate the overall appearance of the new *Celosia,* showing the colors as true as it is reasonably possible to obtain in colored reproductions of this type. Colors in the photographs may differ slightly from the color values cited in the detailed botanical description which accurately describe the colors of the new *Celosia.*

The photograph on the first sheet comprises a side perspective view of a typical flowering plant of 'Zancelor' grown in a container.

The photograph on the second sheet is a close-up view of typical leaves and inflorescences of 'Zancelor'.

DETAILED BOTANICAL DESCRIPTION

The aforementioned photograph and following observations, measurements and values describe plants grown during the autumn in Rijsenhout, The Netherlands in containers and under commercial practice in a glass-covered greenhouse with day and night temperatures ranging from 20° C. to 22° C. Plants were pinched one time. Plants had been growing for about four months when the photographs and description were taken. In the following description, color references are made to The Royal Horticultural Society Colour Chart, 2001 Edition, except where general terms of ordinary dictionary significance are used.

Botanical classification: *Celosia argentea* cultivar Zancelor.

Parentage: Self-pollination of a proprietary selection of *Celosia argentea* identified as code number 00014-2, not patented.

Propagation:

*Type.*—By cuttings.

*Time to initiate and develop roots.*—About 9 to 14 days.

*Root description.*—Fine, fibrous; greyed brown, 199D, in color.

*Rooting habit.*—Freely branching; dense.

Plant description:

*Plant form/habit.*—Herbaceous annual typically grown as a potted plant. Upright and compact plant habit; narrow inverted triangle. Freely branching habit; about four to five lateral branches per plant developed when pinched. Moderate vigor.

*Plant height.*—About 30 cm.

*Plant width* (*spread*).—About 19 cm.

*Lateral branches.*—Length: About 28 cm. Diameter: About 3 mm to 4 mm. Internode length: About 2 cm to 3 cm. Texture: Smooth, glabrous. Color: 199C; towards the base, 50A.

Foliage description:

*Arrangement.*—Alternate; simple.

*Length.*—About 5 cm to 14 cm.

*Width.*—About 1.5 cm to 6 cm.

*Shape.*—Elliptic to lanceolate.

*Apex.*—Apiculate.

*Base.*—Attenuate.

*Margin.*—Entire.

*Texture, upper and lower surfaces.*—Smooth, glabrous.

*Venation pattern.*—Pinnate.

*Color.*—Developing leaves, upper surface: Close to 143B. Developing leaves, lower surface: 134B. Fully expanded leaves, upper surface: 138A; random sectors and spots, N170B; venation, 159C. Fully expanded leaves, lower surface: 143A; venation, 143C.

*Petiole length.*—About 1.5 cm to 2 cm.

*Petiole diameter.*—About 3 mm.

*Petiole texture, upper and lower surfaces.*—Smooth, glabrous.

*Petiole color, upper surface.*—159C.

*Petiole color, lower surface.*—143C.

Flower description:

*Flower type/habit.*—Single tubular flowers arranged in terminal plume-like spikes; flowers face mostly upright. Freely flowering habit, about 1,000 flowers per inflorescence; inflorescences dense.

*Fragrance.*—None detected.

*Natural flowering season.*—Continuously flowering during the summer in The Netherlands. Flowers persistent.

*Postproduction longevity.*—Inflorescences last about two to three months on the plant.

*Inflorescence height.*—About 5 cm to 6 cm.

*Inflorescence diameter.*—About 2.5 cm to 3 cm.

*Flower diameter.*—About 2 mm.

*Flower depth.*—About 8 mm.

*Petals.*—None observed.

*Sepals.*—Quantity per flowers: Typically ten. Length: About 2 mm to 3 mm. Width: About 1 mm. Shape: Lanceolate. Apex: Apiculate. Margin: Entire. Texture, upper and lower surfaces: Smooth, glabrous. Color: When opening and fully opened, upper surface: N30D. When opening and fully opened lower surface: 11C.

*Pedicels.*—Length: About 1 mm to 5 mm. Diameter: About 1 mm to 1.5 mm. Angle: About 30° from vertical. Strength: Weak; flexible. Texture: Smooth, glabrous. Color: 11C.

*Reproductive organs.*—Stamens: Quantity per flower: Typically five. Anther color: Close to 160A. Anther shape: Elliptic. Anther length: About 1 mm. Pollen amount: Scarce. Pollen color: Close to 13A. Pistils: Quantity per flower: One. Stigma color: Close to 154D. Style length: About 8 mm. Style color: Close to 154C. Ovary color: Close to 145D.

*Seeds.*—Length: About 1 mm. Diameter: About 1 mm. Color: 202A.

Disease/pest resistance: Plants of the new *Celosia* have not been noted to be resistant to pathogens and pests common to *Celosia*.

Garden performance: Plants of the new *Celosia* have been observed to have good garden performance and tolerate rain, wind and temperatures ranging from about 5° C. to 35° C.

It is claimed:

1. A new and distinct *Celosia* plant named 'Zancelor' as illustrated and described.

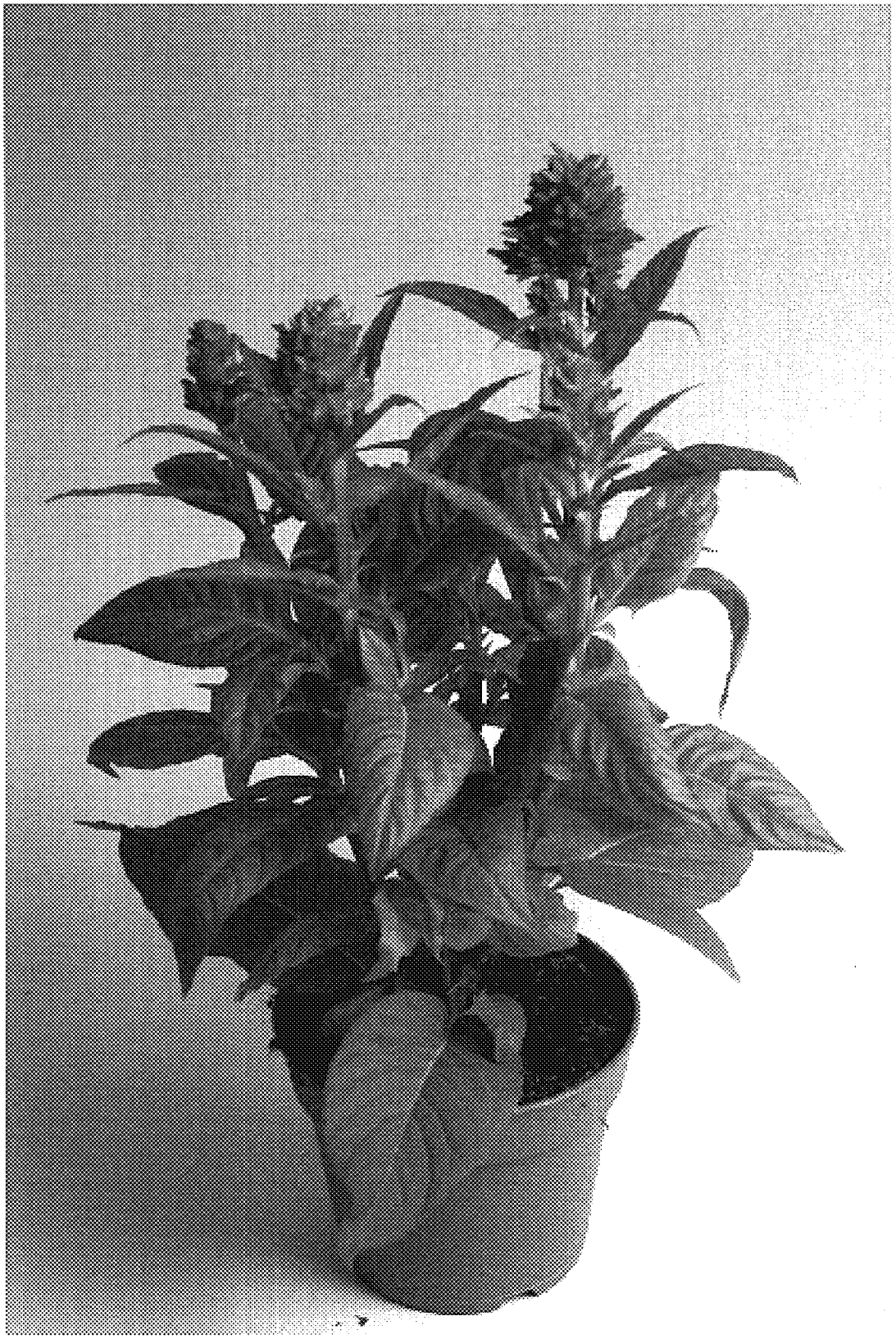

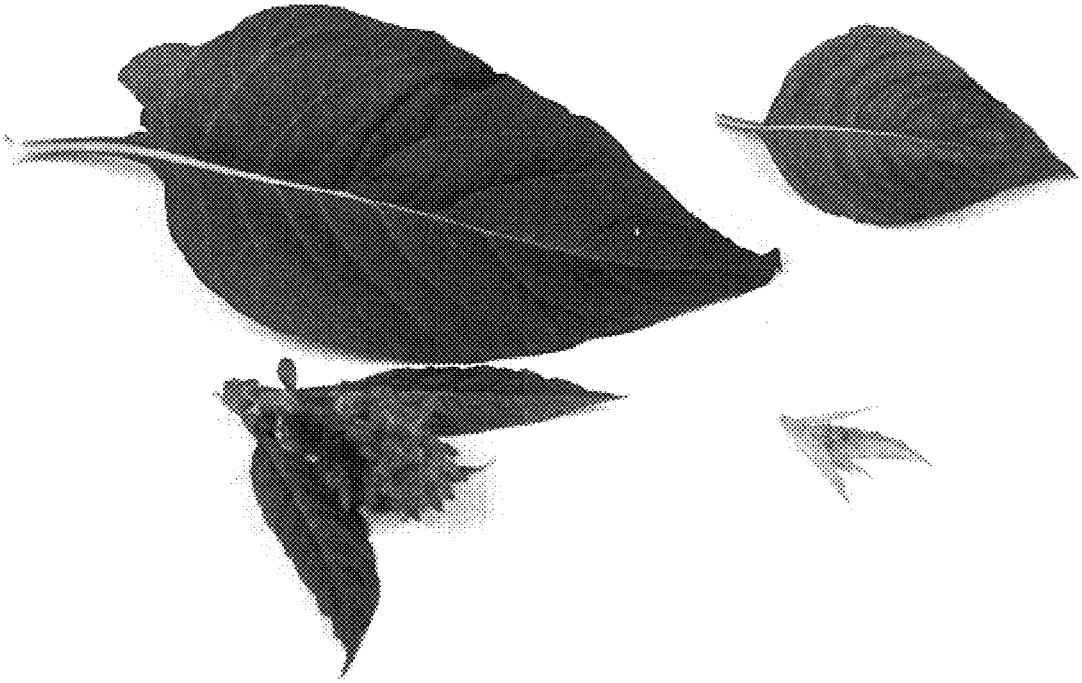

* * * * *